United States Patent [19]

Weithmann et al.

[11] Patent Number: 4,983,514
[45] Date of Patent: Jan. 8, 1991

[54] METHOD FOR DETECTING THE ANTIAGGREGATORY EFFECT OF VASOACTIVE SUBSTANCES, SPECIFICALLY OF INHIBITORS OF PHOSPHODIESTERASE AND/OR CYCLOOXYGENASE

[75] Inventors: Klaus U. Weithmann, Hofheim am Taunus; Dirk Seiffge, Münzenberg, both of Fed. Rep. of Germany

[73] Assignee: Hoechst Aktiengesellschaft, Frankfurt am Main, Fed. Rep. of Germany

[21] Appl. No.: 196,600

[22] Filed: May 20, 1988

[30] Foreign Application Priority Data

May 22, 1987 [DE] Fed. Rep. of Germany ....... 3717337

[51] Int. Cl.$^5$ .......................... C12Q 1/02; C12Q 1/56
[52] U.S. Cl. ......................................... 435/29; 435/13; 435/19; 435/25; 435/184; 436/63; 436/69
[58] Field of Search ..................... 435/13, 19, 25, 184, 435/810

[56] References Cited

U.S. PATENT DOCUMENTS 4,051,236 9/1977 Harris et al. .
4,694,024 9/1987 Weithmann et al. .

FOREIGN PATENT DOCUMENTS 0169465 7/1985 European Pat. Off. .
0208962 6/1986 European Pat. Off. .
3508097A1 2/1980 Fed. Rep. of Germany .
3515874A1 1/1986 Fed. Rep. of Germany .
3524051A1 1/1987 Fed. Rep. of Germany .
3526362A1 1/1987 Fed. Rep. of Germany .
85/5457 7/1985 South Africa .
85/5395 7/1986 South Africa .
87/00434 1/1987 World Int. Prop. O. .

OTHER PUBLICATIONS

Smith, "Effect of Thromboxane Synthetase Inhibitors . . . ", *Thrombosis Research*, 28:477–485 (1982).
Born, G. V. R., "Aggregation of Blood Platelets by Adenosine Diphosphate and Its Reversal", Nature, 194:927–929 (1962).
Ingerman-Wojenski et al., "Evaluation of Electrical Aggregometry: Comparision with Optical Aggregometry, Secretion of ATP, and Accumulation of Radiolabeled Platelets", J. Lab. Clin. Med., 101:44–52 (1983).
M. Chignard et al., "The Role of Platelet-Activating Factor in Platelet Aggregation," Nature, vol. 279, 5716, pp. 799–800, (Jun. 28, 1979).
M. Kuchar and V. Rejholec, "Antithrombotic Agents," Drugs of the Future, vol. 11, No. 8, pp. 689–701 (1986).
Ser. No. 06/881,658 filed 07/03/1986 under Weithmann et al.

*Primary Examiner*—Sam Rosen
*Attorney, Agent, or Firm*—Finnegan, Henderson, Farabow, Garrett, and Dunner

[57] ABSTRACT

The antiaggregatory effect of phosphodiesterase inhibitors (A) and/or of cyclooxygenase inhibitors (B) is detected outside the human or animal body by sampling blood, addition of (A) and/or (B) to the blood sample—if not already present therein, in unchanged or in metabolized form, as a consequence of previous administration, where appropriate removal of the erythrocytes and leukocytes and initiation—preferably by addition of an aggregation inducer—and measurement of the platelet aggregation, the method comprises (A) also being added—if only (B) has been administered or added up till then—or (B) also being added—if only (A) has been administered or added up till then—and at least one prostaglandin (C) being added, before, or no later than at, the initiation of the platelet aggregation, so that the initiation and measurement of the platelet aggregation takes place in the presence of the ternary combination of (A), (B), each in the unchanged or in metabolized form, and (C).

Suitable as (A) are preferably compounds with a xanthine or pyrimidopyrimidine structure and as (B) is preferably O-acetylsalicylic acid. The method replaces elaborate and complicated tests on the human and animal body.

10 Claims, No Drawings

METHOD FOR DETECTING THE ANTIAGGREGATORY EFFECT OF VASOACTIVE SUBSTANCES, SPECIFICALLY OF INHIBITORS OF PHOSPHODIESTERASE AND/OR CYCLOOXYGENASE

The formation of platelet aggregates on the blood vessel wall is regarded as an important step in the pathogenesis of thrombotic disorders. The biochemical reaction pathways which result in platelet aggregation have already been thoroughly investigated and described.

Platelet aggregation can be initiated by certain stimulators, for example by arachidonic acid $CH_3(CH_2)_4(CH=CHCH_2)_4(CH_2)_2COOH$. In the platelets, this polyunsaturated fatty acid is converted by the enzyme cyclooxygenase into prostaglandin endoperoxide and further into thromboxane $A_2$, both of which are extremely effective inducers of platelet aggregation. Platelet aggregation can also be induced by other substances which, like collagen, catalyze, for example, the release of intracellular arachidonic acid from lipid fractions of the platelets.

The induced aggregation of platelets can be inhibited with the aid of inhibitors of the cyclooxygenase enzyme. Inhibitors of this type have already been disclosed. The experimentally and clinically detectable aggregation-inhibiting and antithrombotic effects of O-acetylsalicylic acid (acetylsalicylic acid) are explained by its inhibitory effect on cyclooxygenase.

Moreover, various representatives of the xanthine and pyrimido-pyrimidine classes of substances are attributed with aggregation-inhibiting and antithrombotic effects. Typical examples are pentoxifylline and dipyridamole; these are the compounds of the formulae

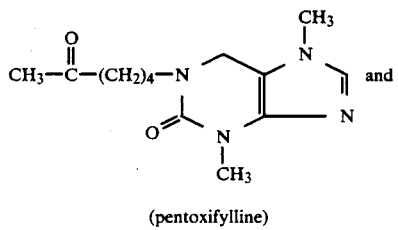

(pentoxifylline)

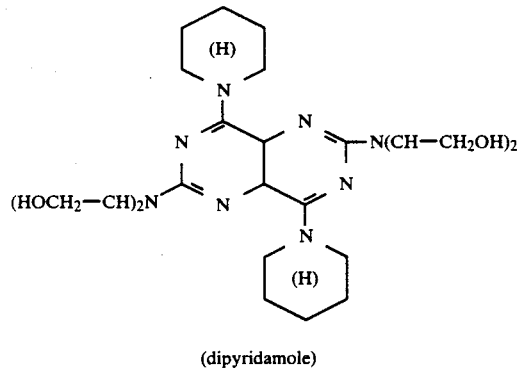

(dipyridamole)

These substances have been described as inhibitors of platelet phosphodiesterase. This enzyme catalyzes the hydrolysis of cyclic adenosine monophosphate (cyclic AMP) to the inactive secondary product 5'-AMP. The decomposition of cyclic AMP is inhibited by inhibiting the enzyme. Thus an increase in cyclic AMP within the platelets may occur, which results in inhibition of platelet aggregation.

The aggregation-inhibiting effect of another class of substances, the prostaglandins, is likewise explained with the aid of cyclic AMP-stimulating mechanisms. One representative example of this class of substances is prostaglandin $I_2$ ($PGI_2$) which has been described as an important metabolite of arachidonic acid in the blood vessel wall.

Rather high concentrations of active substance are necessary for the detection of the aggregation-inhibiting effect of the xanthines and of the pyrimido-pyrimidines in vitro, as well as of the cyclooxygenase inhibitors, such as acetylsalicylic acid.

Detection of the effect in animals can be carried out in various ways, namely by investigation of the blood ex vivo or in vivo by suitable invasive techniques. In the ex vivo experiment, blood is taken from the animal after administration of the active substance, which can be carried out in a customary manner, for example orally or intravenously, and platelet aggregation is induced outside the animal body mechanically or with the aid of the known inducers. The measurand which is determined is the tendency of the platelets to aggregate (aggregability); suitable methods of measurement are described by, for example, G. V. R. Born in Nature Vol. 194 (1962), 927 (optical measurement in blood plasma) and by C. Ingerman-Wolenski et al. in J. Lab. Clin. Med., January 1983, Vol. 101, No. 1, 44 (measurement of the electrical resistance in whole blood). This ex vivo technique can also be applied to investigations on humans without difficulty. In this connection, however, it is a great disadvantage that the aggregation-inhibiting effect of the medicaments can be detected only after relatively high doses.

It is true that invasive techniques can be used to detect the desired effect of the medicaments in vivo after lower doses. However, for obvious reasons, these techniques, which include, for example, induction of thromboses by irritation of the blood vessel wall (for example using a laser beam or electrically or mechanically), cannot be applied to humans. Hence, for accurate clinical assessment of vasoactive medicaments it is necessary to carry out long-term observations on a large number of patients at risk of thrombosis (for example atherosclerotic patients or patients who have had an infarct or vascular surgery) for the occurrence of thrombotic events.

It has now been found, in experiments on human blood taken from the veins of volunteers, that the inhibition of platelet aggregation was greater when the vessel wall metabolite $PGI_2$ was also added ex vivo to the blood (or plasma) of blood donors who had previously been treated with vasoactive medicaments, such as xanthines (for example pentoxifylline) or pyrimido-pyrimidines, or other inhibitors of phosphodiesterase. This effect was all the more surprising because it was even achieved with $PGI_2$ concentrations which themselves do not bring about any inhibition of platelet aggregation. It was thus still more surprising that, by subsequent addition ex vivo of $PGI_2$ and a cyclooxygenase inhibitor, such as acetylsalicylic acid, an additional drastic inhibition of platelet aggregation was observed and was far beyond that achieved by addition of the cyclooxygenase inhibitor alone, that is to say without $PGI_2$. The necessary blood or plasma levels of acetylsalicylic acid can, of course, be obtained not only by (the) subsequent addition of this medicament ex vivo but also by treatment of the test subject with this medicament, for example orally. Conversely, the blood or plasma can also be mixed directly in vitro with phosphodiesterase inhibitors.

Surprisingly, it is also possible to replace $PGI_2$ in this by other prostaglandins such as $PGE_1$, $PGD_2$ or derivatives thereof. This is a great advantage because these prostaglandins, especially $PGE_1$ and $PGD_2$, are more chemically stable than $PGI_2$, which becomes biologically inactive within minutes at physiological pH due to hydrolysis.

Hence the invention relates to a method for detecting the antiaggregatory effect of phosphodiesterase inhibitors (A) and/or cyclooxygenase inhibitors (B) outside the human or animal body by
sampling blood,
addition of the phosphodiesterase inhibitor (A) and/or cyclooxygenase inhibitor (B) which is to be tested to the blood sample—if not already present therein, in unchanged or in metabolized form, as a consequence of previous administration,
where appropriate removal of the erythrocytes and leukocytes and
initiation—preferably by addition of an aggregation inducer—and measurement of the platelet aggregation;
the method comprises a phosphodiesterase inhibitor (A) also being added—if only a cyclooxygenase inhibitor (B) has been administered or added up till then—or a cyclooxygenase inhibitor (B) also being added—if only a phosphodiesterase inhibitor (A) has been administered or added up till then—and at least one prostaglandin (C) being added, before, or no later than at, the initiation of the platelet aggregation, so that the initiation and measurement of the platelet aggregation takes place in the presence of the ternary combination of phosphodiesterase inhibitor (A), cyclooxygenase inhibitor (B), each in the unchanged or in metabolized form, and prostaglandin (C).

It has already been concluded from the superadditive antiaggregatory effect, which has already been disclosed, of binary combinations composed of certain phosphodiesterase inhibitors (xanthines) or the cyclooxygenase inhibitor acetylsalicylic acid and certain heteroiminoprostacyclins that a medicament composed of the ternary combination of certain xanthines, acetylsalicylic acid and certain heteroiminoprostacyclins may have therapeutic benefits (cf. DE-A-No. 3,524,051). However, the even greater—compared with the relevant binary combinations—superadditive antiaggregatory effect of the ternary combination of phosphodiesterase inhibitor, cyclooxygenase inhibitor and prostaglandin has only now been recognized for the first time and is the basis of the present invention.

The value of the method according to the invention primarily derives from the fact that, because of the opportunity which it provides for detecting the antiaggregatory effect of phosphodiesterase inhibitors and cyclooxygenase inhibitors outside the human or animal body, elaborate and complicated series of tests on humans and animals have been and are made redundant. The invention was worked out with pentoxifylline as phosphodiesterase inhibitor and with acetylsalicylic acid as cyclooxygenase inhibitor, the antiaggregatory effect thereof being known; however, application to other phosphodiesterase inhibitors and cyclooxygenase inhibitors functions in an identical manner and then also allows comparison with, for example, the antiaggregatory effect of pentoxifylline and acetylsalicylic acid (see the experimental section).

In principle, the method can be carried out with all possible phosphodiesterase inhibitors, cyclooxygenase inhibitors and prostaglandins; however, it is preferably carried out with the following compounds:

Phosphodiesterase inhibitors (A)

compounds with a xanthine structure or with a pyrimido-pyrimidine structure; principally
(a) xanthine derivatives of the type described in DE-A-No. 3,508,097, that is to say compounds of the formula I

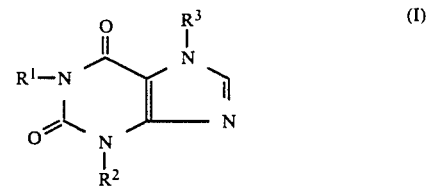

in which one of the radicals $R^1$ and $R^3$ represents a straight-chain alkyl, ($\omega$-1)-oxyalkyl or ($\omega$-1)-hydroxyalkyl group having 3 to 8 carbon atoms, and the other two radicals $R^2$ and $R^3$ or $R^1$ and $R^2$ represent straight-chain or branched alkyl groups having 1 to 8 carbon atoms in the position of $R^1$ and $R^3$ and having 1 to 4 carbon atoms in the position of $R^2$, with the total of the carbon atoms in these two alkyl substituents not exceeding 10, (b) compounds of the formula I with $R^1$, $R^2$ and $R^3$ being, independently of one another, H or $C_1$-$C_4$-alkyl (that is to say unsubstituted xanthine, caffeine, theobromine, theophylline etc.)

(c) xanthine derivatives of the type described in DE-A-No. 3,508,097 and of the formula Ia:

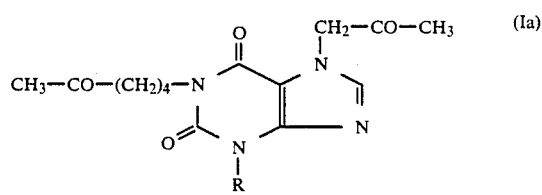

in which R=$C_1$-$C_4$-alkyl, (d) prodrug forms, biologically active metabolites of the compounds mentioned under a, b and c, and the salts thereof.

(e) pyrimido-pyrimidines of the type mentioned in DE-A-No. 3,515,874 and of the formula III:

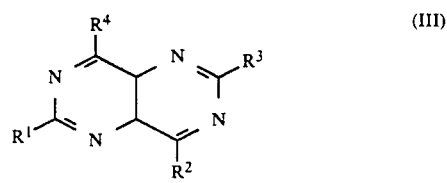

in which at least one of the radicals
$R^1$ and $R^3$ is $N(CH_2-CHR^5-OH)_2$, and $R^5$ is H or $CH_3$,
and at least one of the radicals $R^2$ and $R^4$ is

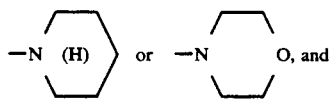

(f) prodrug forms and biologically active metabolites of the compounds of the formula III, and the salts thereof.

Cyclooxygenase inhibitors (B)

O-acetylsalicylic acid, indomethacin (=No. 4852 in "The Merck Index", Rahway/U.S.A., 10th edition 1983)

metamizol (=No. 3369 in the abovementioned Merck Index) and ibuprofen (=No. 4797 in the abovementioned Merck Index)

and the prodrug forms, biologically active metabolites and salts thereof.

Prostaglandins (C)

the compounds mentioned in DE-A-No. 3,526,362, page 3, lines 21-59, specifically prostaglandin $E_1$, 6-keto-$PGE_1$, $PGI_2$ and $PGD_2$, as well as the salts and derivatives thereof.

Particularly preferred phosphodiesterase inhibitors (A), cyclooxygenase inhibitors (B) and prostaglandins (C) are:

Phosphodiesterase inhibitors (A)

pentoxifylline (=compound of the formula I with $R^1 = -(CH_2)_4-CO-CH_3$ and
$R^2 = R^3 = CH_3$), dipyridamole (=compound of the formula III with $R^1 = R^3 = -N(CH_2-CH_2OH)_2$ and

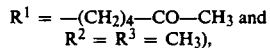

mopidamol (=compound of the formula III with $R^1 = R^3 = -N(CH_2-CH_2OH)_2,$
$R^2 = H$ and

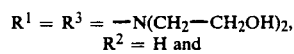

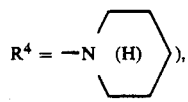

as well as the salts of the two latter compounds.

Cyclooxygenase inhibitors (B)

O-acetylsalicylic acid

Prostaglandins (C)

prostaglandin $E_1$ and 6-keto-prostaglandin $E_1$.

The phosphodiesterase inhibitors (A) and cyclooxygenase inhibitors (B) to be investigated can be administered to the human or animal body, singly or in combination—for example orally—or can be added to the blood sample only after blood sampling.

It is of course also possible to administer the substances in prodrug form, in the form of biologically active metabolites or as salts. If the salts are administered to the human or animal body, care must be taken that they are physiologically acceptable. However, if the salts are added to the blood sample only after blood sampling, they no longer need to be physiologically acceptable.

The addition of at least one prostaglandin (C) normally takes place after the blood sampling. The only point which has always to be taken into account is that the ternary combination of phosphodiesterase inhibitor (A), cyclooxygenase inhibitor (B), each in the unchanged or in metabolized form, and prostaglandin (C) is present before, or no later than at, the initiation of platelet aggregation.

The concentration ranges preferred for this purpose are the following:

Phosphodiesterase inhibitor (A): about $10^{-8}$ to $10^{-3}$ mol/l, in particular about $10^{-6}$ to $10^{-4}$ mol/l;

Cyclooxygenase inhibitor (B): same concentration range as for (A);

Prostaglandin (C): about $10^{-10}$ to $10^{-6}$ mol/l, in particular about $10^{-9}$ to $10^{-7}$ mol/l.

The concentration ranges indicated here are essentially only indicative. It may be expedient, depending on the activity of the individual substances, to operate more in the lower part (with high activity) or more in the upper part (with lower activity) of the concentration range.

The initiation of aggregation induction and the measurement of platelet aggregation are carried out by methods known per se. Thus, for example, it is possible first to remove the erythrocytes and leukocytes by centrifugation, and then to initiate (mechanically or, preferably, by addition of an aggregation inducer such as arachidonic acid or collagen) and to measure optically the platelet aggregation in the remaining blood plasma, or the aggregation induction can also be carried out in whole blood, and the aggregation therein can then be measured electrically, for example.

Chemical initiation of platelet aggregation with arachidonic acid or collagen, and optical measurement of the aggregation in the blood plasma, are preferred.

EXPERIMENTAL SECTION

Methods

Induced Aggregation of Human Platelets In Vitro—Ex Vivo

Blood is taken, by careful cannulation of the antecubital vein, from apparently healthy male and female volunteers who have taken no medicaments in the preceding 10-day period (for exception, see Example 1), and is immediately stabilized with sodium citrate (ad 0.38%). Centrifugation at $140 \times g$ (g=acceleration due to gravity) for 15 minutes results in platelet-rich plasma (PRP) in the supernatant, whose platelet content ought to be in the range $2.5-3.5 \times 10^8$/ml (Coulter counter). Platelet aggregation is followed optically by measurement of the light transmission in a Born aggregometer. The total volume of the test mixture is 0.25 ml. The preincubation with the test product at 37° C. lasts 10 min, and aggregation is then induced with $2 \times 10^{-4}$ mol/l arachidonic acid or 2.4 pg/ml collagen. Each of the test products is tested on five different donors. Dose-effect curves are constructed from the maximum aggregation amplitudes in each case, and the arithmetic means of the $ED_{50}$ (mol/l) are determined graphically ($ED_{50}$=concentration necessary for 50% inhibition).

EXAMPLE 1

1. Human Study Ex Vivo 25 ml of antecubital blood were taken from a volunteer subject and used to prepare citrated plasma in the usual way (see methods) for the control (comparison) measurements.

Immediately after blood sampling the subject was treated orally with 600 mg of pentoxifylline (Trental ® 600, from Albert Roussel Pharma GmbH, Wiesbaden). 80 minutes later, a further 25 ml of blood were taken and used to prepare, as described above, citrated plasma for the active drug test. The samples were incubated at 25° C. and then collagen was added to the control plasma and to the active drug plasma, and platelet aggregation was measured as described above (for control test, see Table 1, Exp. I).

Then $5.5 \times 10^{-8}$ mol/l $PGE_1$ or $1.1 \times 10^{-5}$ mol/l O-acetylsalicylic acid were added to the relevant plasma (for incubation times, see parentheses in table). Virtually unhindered platelet aggregation could be initiated in this case too (Exp. II and III). Although acetylsalicylic acid and $PGE_1$ are known to be inhibitors of platelet aggregation, in these concentrations they bring about virtually no inhibition, that is to say the measured aggregation is complete (=0% inhibition of aggregation) or virtually complete.

Results

| Experiment | | Inhibition of aggregation |
|---|---|---|
| | (A) Control Test (untreated subject) | |
| I | without medicament addition ex vivo | 0% |
| II | $1.1 \times 10^{-5}$ mol/l acetylsalicylic acid (10 min) | 2% |
| III | $5.5 \times 10^{-8}$ mol/l prostaglandin $E_1$ (15 min) | 12% |
| IV | $1.1 \times 10^{-5}$ mol/l acetylsalicylic acid (10 min) + $5.5 \times 10^{-8}$ mol/l prostaglandin $E_1$ (15 min) | 63% |
| V | $7.2 \times 10^{-5}$ mol/l pentoxifylline (25 min) | 0% |
| VI | $7.2 \times 10^{-5}$ mol/l pentoxifylline (25 min) + $5.5 \times 10^{-8}$ mol/l prostaglandin $E_1$ (15 min) | 21% |
| | (B) Active drug test (subject treated with pentoxifylline) | |
| VII | no additions | 4% |
| VIII | $1.1 \times 10^{-5}$ mol/l acetylsalicylic acid (10 min) | 23% |
| IX | $5.5 \times 10^{-8}$ mol/l prostaglandin $E_1$ (15 min) | 27% |
| X | $1.1 \times 10^{-5}$ mol/l acetylsalicylic acid (10 min) + $5.5 \times 10^{-8}$ mol/l prostaglandin $E_1$ (15 min) | 91% |

(All the measurements are related to Exp. I = 0% inhibition of aggregation, i.e. complete aggregation)

Comparison of, in particular, Experiment I with VII shows that aggregation ex vivo is changed to only a small extent after oral treatment of the subject with pentoxifylline. However, the inhibitory effect of pentoxifylline on aggregation ex vivo becomes evident when $PGE_1$ is added ex vivo to the platelet system (Exp. III vs. IX). The inhibitory effect becomes even greater (cf. Exp. IV vs. X) when $PGE_1$ and acetylsalicylic acid are added ex vivo.

Similar antiaggregatory effects ex vivo are obtained in humans when the subject who has been treated orally with pentoxifylline is also treated orally with acetylsalicylic acid, and the blood plasma is mixed with $PGE_1$ ex vivo before determination of the platelet aggregation.

The aggregation experiments which are described hereinafter were carried out as described under "Methods" in vitro with human plasma.

Before induction of aggregation, the plasma was incubated in vitro with the phosphodiesterase inhibitor (A) for 20 min, with the cyclooxygenase inhibitor (B) for 10 min and with the prostaglandin (C) for 25 min. The comparison experiments according to the state of the art were carried out correspondingly with one or with two of the said classes of active substances in each case. (The numbering of the experiments is unrelated to that of those on the preceding pages).

| | | % Inhibition of aggregation by single substances |
|---|---|---|
| Phosphodiesterase inhibitors (A) | | |
| VI | $5.3 \times 10^{-5}$ mol/l dipyridamole | 3 |
| VII | $1.0 \times 10^{-5}$ mol/l mopidamol | 4 |
| VIII | $7.2 \times 10^{-5}$ mol/l pentoxifylline | 0 |
| IX | $1.2 \times 10^{-4}$ mol/l pentoxifylline | 5 |
| X | $2.0 \times 10^{-4}$ mol/l pentifilline | 7 |
| XI | $2.0 \times 10^{-4}$ mol/l propentofylline (= 1-(5-oxohexyl)-3-methyl-7-propylxanthine) | 6 |
| XII | $7.5 \times 10^{-5}$ mol/l 3,7-dimethyl-1-(3-carboxypropyl)xanthine (metabolite of pentoxifylline) | 2 |
| XIII | $7.5 \times 10^{-5}$ mol/l 3,7-dimethyl-1-(5-hydroxyhexyl)xanthine (metabolite of pentoxifylline) | 0 |
| XIV | $4.4 \times 10^{-4}$ mol/l theophylline | 8 |
| Cyclooxygenase inhibitors (B) | | |
| I | $1.1 \times 10^{-5}$ mol/l acetylsalicylic acid | 0 |
| II | $5.5 \times 10^{-5}$ mol/l acetylsalicylic acid | 15 |
| III | $5.6 \times 10^{-7}$ mol/l indomethacin | 0 |
| IV | $9.2 \times 10^{-7}$ mol/l methylaminoantipyrine (metabolite of metamizole) | 2 |
| V | $9.7 \times 10^{-7}$ mol/l ibuprofen | 5 |
| Prostaglandins (C) | | |
| XV | $2.0 \times 10^{-10}$ mol/l $PGI_2$ | 0 |
| XVI | $2.0 \times 10^{-8}$ mol/l $PGE_1$ | 7 |
| XVII | $5.0 \times 10^{-8}$ mol/l $PGE_1$ | 10 |

| % Inhibition of aggregation | | | |
|---|---|---|---|
| by combinations of the state of the art | | by combinations according to the invention | |
| I + VI | 3 | I + VI + XV | 89 |
| I + VII | 5 | I + VII + XVI | 92 |
| I + VIII | 1 | I + VIII + XVI | 87 |
| I + IX | 5 | I + IX + XVI | 91 |
| I + X | 8 | I + X + XVII | 95 |
| I + XI | 7 | I + XI + XV | 91 |
| I + XII | 3 | I + XII + XVI | 92 |
| I + XIII | 2 | I + XIII + XV | 85 |
| I + XIV | 10 | I + XIV + XVII | 97 |
| I + XV | 10 | | |
| I + XVI | 10 | | |
| I + XVII | 13 | | |
| II + VI | 18 | II + VI + XVI | 88 |
| II + IX | 22 | II + IX + XVI | 89 |
| II + XVI | 31 | | |
| III + VI | 3 | III + VI + XVI | 87 |
| III + VIII | 2 | III + VIII + XVI | 85 |
| III + XVI | 11 | | |
| IV + VIII | 2 | IV + VIII + XVI | 82 |
| IV + XVI | 12 | | |
| V + VII | 10 | V + VII + XV | 84 |
| V + IX | 7 | V + IX + XVII | 87 |
| V + XV | 11 | | |
| V + XVII | 18 | | |
| VI + XV | 5 | | |
| VII + XVI | 15 | | |
| IX + XVI | 16 | | |
| XIV + XVII | 21 | | |
| XI + XV | 9 | | |

We claim:

1. A method for detaching the antiaggregatory effect of photophodiesterase inhibitors (A), cyclooxygenase inhibitors (B), or a mixture of inhibitors (A) and (B), outside the human or animal body in the presence of prostaglandin (C) comprising the steps of:
   i. obtaining a blood sample,
   ii. adding phosphodiesterase inhibitor (A), cyclooxygenase inhibitor (B), or a mixture of inhibitors (A) and (B), when they are not already present in said blood sample in either the unchanged or the metabolized form as consequence of having been administered to the subject human or animal body prior to said blood sampling, and
   iii. adding at least one prostaglandin (C) before or no later than the start of the initiation of the platelet aggregation, and
   iv. initiating and measuring the platelet aggregation.

2. The method as claimed in claim 1, wherein compounds with a xanthine structure or with a pyrimido-pyrimidine structure are used as phosphodiesterase inhibitors (A).

3. The method as claimed in claim 1, wherein said phosphodiesterase inhibitors (A) comprise:
   (a) xanthin derivatives of the formula I $$\text{(I)}$$

in which one of the radicals $R^1$ or $R^3$ represents a straight-chain alky, ($\omega$-1)-oxyalkyl or ($\omega$-1)-hydroxyalkyl group having 3 to 8 carbon atoms, and the other two radicals $R^2$ and $R^3$ or $R^1$ and $R^2$ represent straight-chain or branched alkyl groups having 1 to 8 carbon atoms in the position of $R^1$ and $R^3$ and having 1 to 4 carbon atoms in the position of $R^2$, with the total of the carbon atoms in these two alkyl substituents not exceeding 10, (b) compounds of the formula I with $R^1$, $R^2$ and $R^3$ being, independently of one another, H or $C_1$-$C_4$-alkyl (c) xanthine derivatives of the formula Ia $$\text{(Ia)}$$

in which $R = C_1$-$C_4$-alkyl, (d) prodrug forms, biologically active metabolites of the compounds mentioned under a, b and c, or the salts thereof, (e) pyrimido-pyrimidines of the formula III $$\text{(III)}$$

in which at least one of the radicals $R^1$ or $R^3$ is $-N(CH_2-CHR^5-OH)_2$, and $R^5$ is H or $CH_3$, and at least one of the radicals $R^2$ or $R^4$ is $$-N\underset{}{\diagup\!\!\diagdown}(H) \quad \text{or} \quad -N\underset{}{\diagup\!\!\diagdown}O,$$

or (f) prodrug forms, biologically active metabolites of the compounds of the formula III, or the salts thereof;

wherein said Cyclooxygenase inhibitors (B) comprise:
O-acetylsalicyclic acid,
indomethacin,
metamizole,
ibuprofen,
the prodrug forms, biologically active metabolites, or the salts thereof; and wherein said Prostaglandins (C) comprise:
prostaglandin (PG)$E_1$, 6-keto-$PGE_1$, $PGI_2$ and $PGD_2$ the salts or derivatives thereof.

4. The method as claimed in claim 1, wherein the following compounds are used as phosphodiestearase inhibitors (A), cyclooxygenase inhibitors (B) and prostaglandins (C): Phosphodiesterase inhibitors (A): pentoxifylline, dipyridamole, mopidamol, as well as the salts of the two latter compounds;
Cyclooxygenase inhibitors (B):
O-acetylsalicylic acid;
Prostaglandins (C):
prostaglandin $E_1$ and 6-keto-prostaglandin $E_1$.

5. The method as claimed in claim 1 wherein the following concentrations are set up:
Phosphodiesterase inhibitor (A): about $10^{-8}$ to $10^{-3}$ mol/l;
Cyclooxygenase inhibitor (B): same concentration range as for phosphodiesterase inhibitor (A);
Prostagladin (C): about $10^{-10}$ to $10^{-6}$ mol/l.

6. The method as claimed in claim 1, wherein platelet aggregation is initiated chemically, and arachidonic acid or collagen is used as aggregation inducer.

7. The method as claimed in claim 1, wherein the platelet aggregation is measured optically in the blood plasma.

8. The method of claim 5 wherein said concentrations are:
Phosphodiesterase inhibitors (A): about $10^{-6}$ to $10^{-4}$ mol/l;
Cyclooxygenase inhibitor (B): same concentration range as phosphoiesterase (A);
Prostaglandin (C): $10^{-9}$ to $10^{-7}$ mol/l.

9. The method of claim 1, wherein the erythocytes and leukocytes are removed from said blood sample.

10. The method of claim 1, wherein the initiation is induced by the addition of an aggregation inducer to said blood sample.

* * * * *